United States Patent [19]

Simioni

[11] Patent Number: 5,227,817
[45] Date of Patent: Jul. 13, 1993

[54] SPECTACLE FRAME WITH DETACHABLE ELEMENTS

[75] Inventor: Luciano Simioni, Montebelluna, Italy
[73] Assignee: Moda Solaris S.p.A., Pederobba, Italy
[21] Appl. No.: 821,372
[22] Filed: Jan. 16, 1992

[30] Foreign Application Priority Data

Jan. 21, 1991 [IT] Italy .................. TV91A-000008

[51] Int. Cl.⁵ .................................................. G02C 1/00
[52] U.S. Cl. ........................................ 351/80; 351/86; 351/138
[58] Field of Search ............... 351/47, 52, 57, 79, 351/80, 131, 138, 158, 62, 86, 137, 44, 49; 2/436, 437

[56] References Cited

U.S. PATENT DOCUMENTS

| | | |
|---|---|---|
| 2,423,539 | 7/1947 | Williams ................................. 2/439 |
| 2,594,395 | 4/1952 | Castelli ................................. 2/439 |
| 3,758,203 | 9/1973 | Lipchik et al. ...................... 351/131 |
| 4,102,566 | 7/1978 | Shelton ............................... 351/131 |
| 4,759,622 | 7/1988 | Schmidthaler ....................... 351/86 |
| 4,878,749 | 11/1989 | McGee ................................ 351/52 |
| 4,951,322 | 8/1990 | Lin ........................................ 2/439 |
| 5,032,017 | 7/1992 | Bollé et al. ......................... 351/138 |

FOREIGN PATENT DOCUMENTS

| | | |
|---|---|---|
| 457706 | 6/1949 | Canada. |
| 1427964 | 12/1964 | France. |
| 2588673 | 4/1987 | France. |
| 2102150 | 1/1983 | United Kingdom. |

Primary Examiner—Bruce Y. Arnold
Assistant Examiner—Hung Xuan Dang
Attorney, Agent, or Firm—Guido Modiano; Albert Josif

[57] ABSTRACT

The spectacle frame with detachable elements comprises an upper bar, to which two temples are hinged; the bar is laterally provided with first temporary engagement seats either for possible elements for ventilation and connection to a lens pair or, alternatively, for connection to a single lens. The upper bar is furthermore provided with second temporary engagement seats for a lower supporting bar for the lens pair or for the single lens. Engagement means furthermore protrude from the upper bar or from the lower bar and removably engage complementarily shaped grip means which are associated with the lower or upper bar. Means are finally provided for allowing the temporary mutual safety locking of the engagement means and of the grip means.

12 Claims, 3 Drawing Sheets

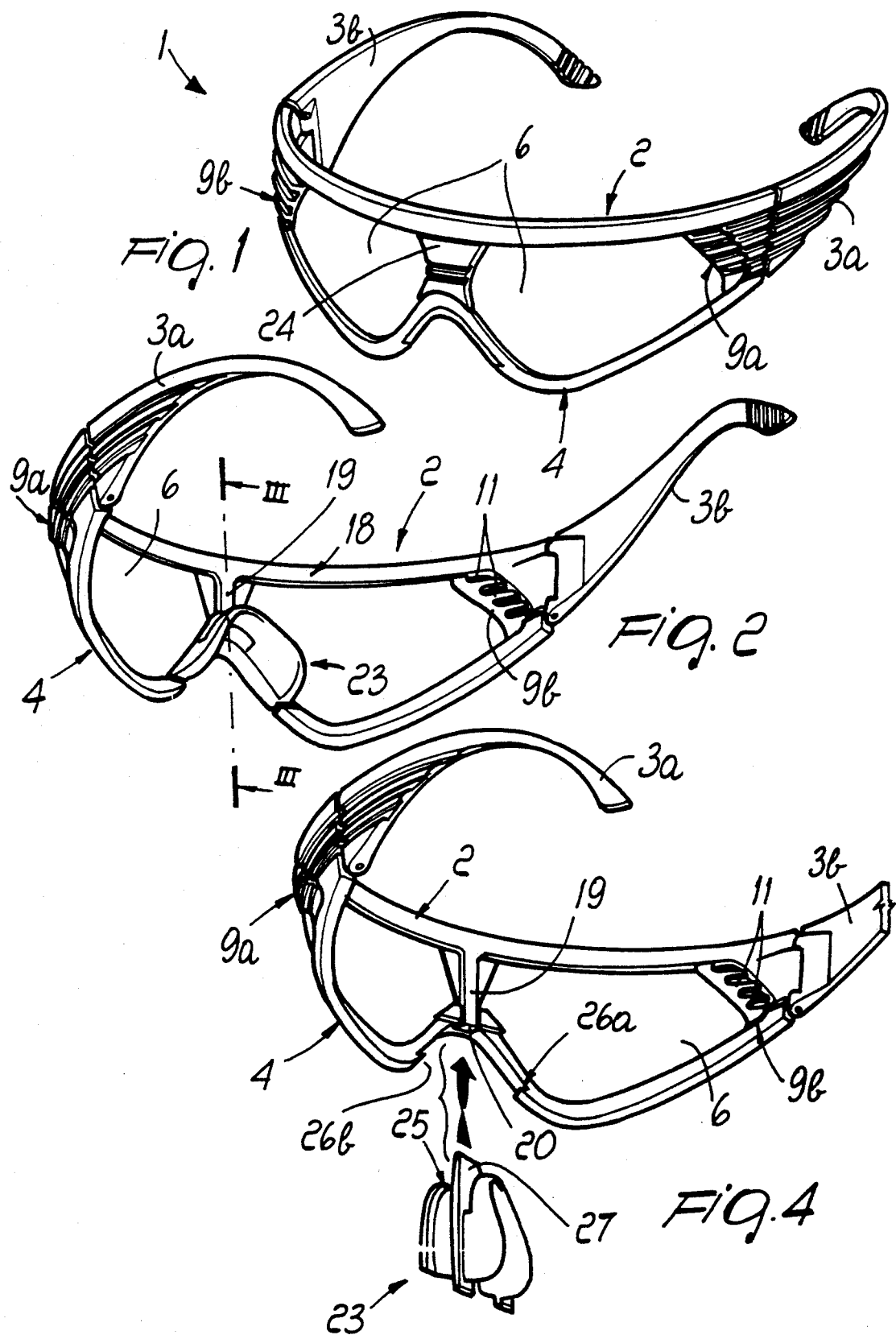

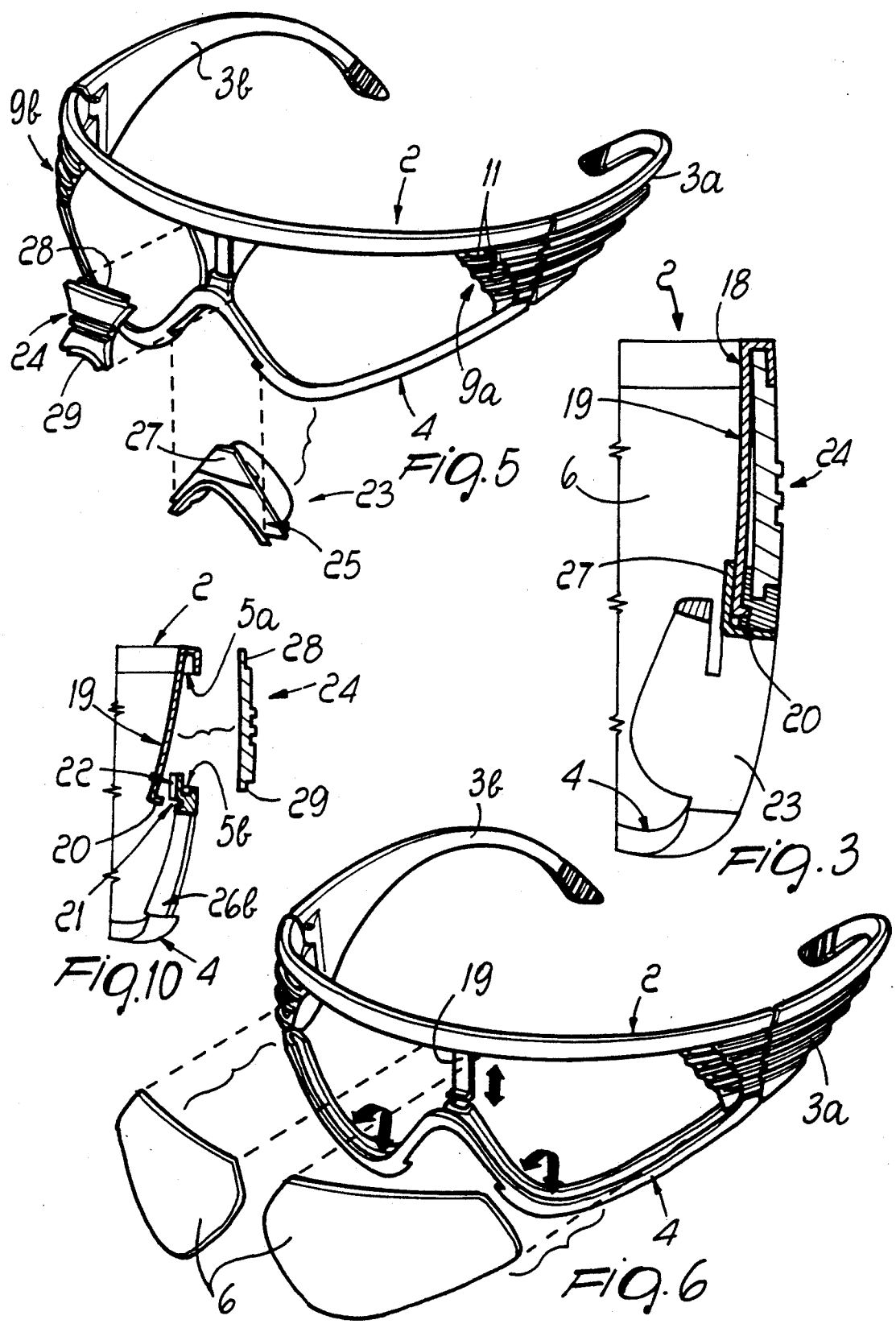

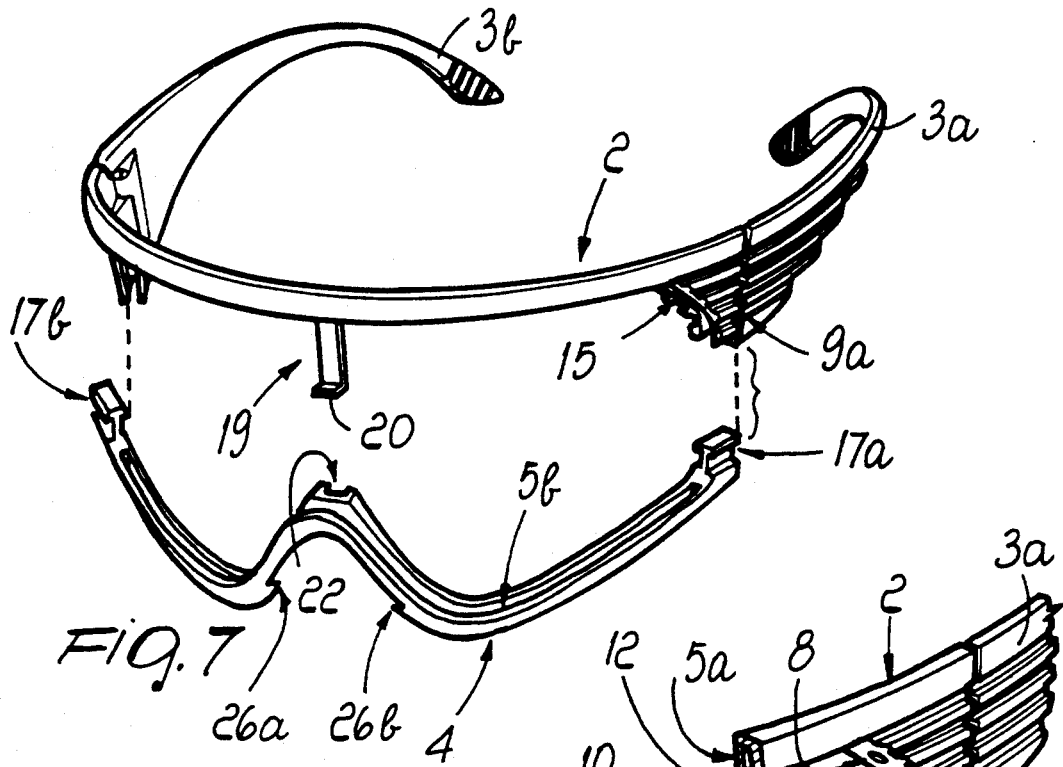
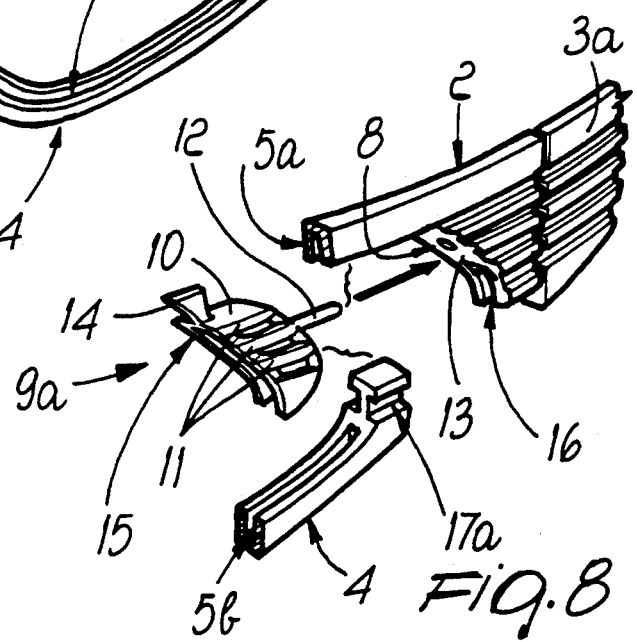
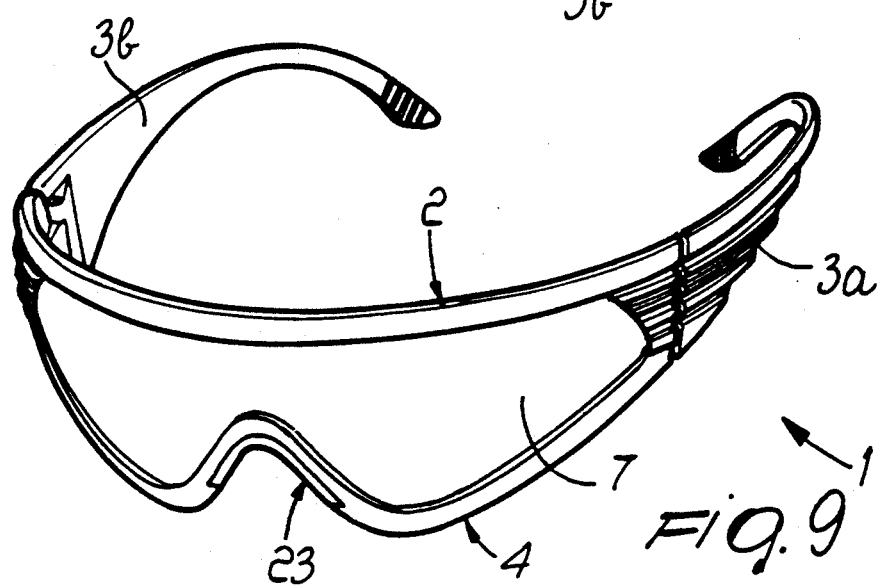

SPECTACLE FRAME WITH DETACHABLE ELEMENTS

BACKGROUND OF THE INVENTION

The present invention relates to a spectacle frame with detachable elements.

In the wide variety of spectacle frames currently known, it is known to provide fronts made of various plastic materials, wherein the lenses are applied by heating said front which, by deforming elastically, allows the insertion and thus the optimum locking of said lenses.

These known types of frame, however, have the problem that they do not allow the user to replace the lenses, and that breakage at any point of the front is necessarily followed by the complete replacement of the frame.

Metallic spectacle frames are furthermore known which are usually constituted by a bar with which containment profiles for lenses are associated or rigidly coupled; said profiles are interrupted at one point, where adapted tubes are in fact associated at their ends and allow to open or close the profiles and thus insert or remove the lenses by means of adapted screws.

Even these known frame types have problems: if the user wishes to replace a lens, he needs special tools, such as screwdrivers with a very narrow flat tip, and he is in any case unable to customize the frame in any way, since replacement of the front, and thus for example of the profiles, is not possible.

SUMMARY OF THE INVENTION

The aim of the present invention is therefore to eliminate the problems described above in known types by providing a spectacle frame which allows a user to rapidly and easily interchange the lenses without requiring particular tools.

Within the scope of the above aim, an important object is to provide a spectacle frame wherein parts of said frame can be replaced by the user in an equally rapid and easy manner in case of breakage thereof or if a different chromatic differentiation of said parts is to be achieved or if the use of lenses with different shapes is desired.

Another important object is to provide an invention which associates with the preceding characteristics that of lo preventing the forming of misting at the lens surface which faces the eye of the user.

A further object is to provide a spectacle frame which is structurally simple and is reliable and safe in use.

This aim, these objects and others which will become apparent hereinafter are achieved by a spectacle frame with detachable elements, characterized in that it comprises an upper bar to which two temples are hinged, said bar being laterally provided with first temporary engagement seats for possible elements for ventilation and connection to a pair of lenses, or for connection to a single lens, and with second temporary engagement seats for a lower supporting bar for said lens pair or single lens, engagement means protruding from said upper or lower bars and removably engaging complementarily shaped grip means associated with said lower or upper bars, means being provided for the temporary mutual safety locking of said engagement means and of said grip means.

BRIEF DESCRIPTION OF THE DRAWINGS

Further characteristics and advantages of the invention will become apparent from the detailed description of a particular but not exclusive embodiment, illustrated only by way of non-limitative example in the accompanying drawings, wherein:

FIG. 1 is a front perspective view of the spectacle frame;

FIG. 2 is a rear perspective view of the spectacle frame;

FIG. 3 is a sectional view, taken along the plane III—III of FIG. 2;

FIG. 4 is a view, similar to FIG. 2, of the spectacle frame, wherein the nose pad has been detached from the lower bar;

FIG. 5 is a front perspective view of the spectacle frame, wherein the nose pad and a central tab which connects the upper bar and the lower bar have been detached;

FIG. 6 is a view, similar to the preceding one, of the spectacle frame, wherein the engagement means have been disengaged from the grip means in order to allow lens replacement;

FIG. 7 is a view, similar to the preceding one, of the condition wherein the lower bar is disengaged from the upper one;

FIG. 8 is a lateral perspective view of a detail related to the coupling between the lower and upper bars and the ventilation elements;

FIG. 9 is a view, similar to FIG. 1, of the spectacle frame with a single lens associated therewith;

FIG. 10 is a view, similar to FIG. 3, of the condition wherein the engagement means are not engaged with the grip means and with a means provided for temporary mutual safety locking.

DESCRIPTION OF THE PREFERRED EMBODIMENTS

With reference to the above figures, the reference numeral 1 designates the spectacle frame, which comprises an upper bar 2; the temples 3a and 3b are hinged to the ends of said upper bar, which is preferably manufactured by injecting thermoplastic material.

The spectacle frame is furthermore constituted by a lower bar 4 which is temporarily associable with the upper bar 2 at the end thereof to which the temples 3a and 3b are hinged.

Both the upper bar 2 and the lower bar 4 have first and second grooves, designated by the numerals 5a and 5b, for temporarily accommodating a lens pair 6 or a single lens 7.

The upper bar 2 is laterally provided, proximate to the end to which the temples 3a and 3b are hinged, with first seats 8 for the temporary engagement of the end of elements, designated by the numerals 9a and 9b, which may be provided for ventilation and connection to the lens pair 6.

Each of said elements 9a and 9b is in fact constituted by a body 10, preferably made of thermoplastic material, which has a plurality of openings 11; a pin 12 protrudes from said body at the end which is associable with the first seats 8 and can be inserted in a complementarily shaped cavity 13 defined within the first seats 8.

In order to allow the optimum mutual association of said elements 9a and 9b and of the first seats 8 of the upper bar 2, a lug 14 protrudes above each body 10 and is slidingly associable at the grooves 5a defined on said upper bar 2.

Naturally, a third groove 15 will be provided on the side opposite to the end provided with the pin 12, in order to allow the positioning of the ends of the lens pair 6 at the elements 9a and 9b.

The ends of the single lens 7 are furthermore associable with the first seats 8, possibly omitting the elements 9a and 9b, as indicated in FIG. 9.

The upper bar 2 is furthermore provided, in a region adjacent to the first seats 8, with second seats 16 for the temporary engagement of the ends of the lower bar 2; a pair of first essentially T-shaped tabs 17a and 17b in fact protrudes from said ends and said tabs slidingly engage within the adapted and complementarily shaped second seats 16.

Engagement means furthermore protrude at the central region of the upper bar 2 from the surface 18 which faces the user's face; said engagement means are constituted by a second wing 19 which is essentially L-shaped and has its shorter arm 20 directed toward the lens pair 6 or the single lens 7.

Said second wing removably engages complementarily shaped grip means which are associated with, or defined at, the lower bar 4: said lower bar in fact has, at the shorter arm 20 of the second wing 19, a third seat 21 which is shaped complementarily thereto, whereas the positioning of the second wing 19 is facilitated by the provision of a fourth groove 22 which is defined transversely to the lower bar 4 and is approximately equal in width to said second wing 19.

The spectacle frame 1 furthermore comprises mean for the mutual temporary safety locking of the second wing 19 and the lower bar 4; said means are constituted by a nose pad 23 and by an insert 24.

The nose pad 23 is made of a soft polymer with which rubber is associated and makes contact with the user's nose; said nose pad is V-shaped and its wings can be elastically compressed.

For this purpose, the nose pad 23 is provided with a fifth groove 25 which is approximately as wide as the lower bar 4; interconnection between the bar 4 and the nose pad 23 occurs by virtue of the provision of a pair of recesses 26a and 26b defined on the lower bar 4. The terminal ends of the nose pad interact with said recesses at the fifth groove 25.

The nose pad 23 is furthermore provided with a third planar tab 27 which protrudes at the arm connecting region and abuts, once the frame has been assembled, at the second wing 19.

The insert 24 can be arranged between the upper bar 2 and the lower bar 4 at the connecting region by virtue of the second wing 19, between said bars, said insert 24 thus having such a shape as to conceal the interspace defined between the bars and the lens pair 6.

Said insert 24 naturally cannot be used if a single lens 7 is used.

The insert 24 is thus provided with a body having ends from which a fourth tab 28 and a fifth tab 29 protrude; said tabs can be temporarily inserted respectively at the first groove 5a defined on the upper bar 2 and in the second groove 5b defined on the lower bar 4 in the region, as mentioned, which faces the second wing 19.

Said insertion is facilitated by the fact that the insert 24 is advantageously made of elastically deformable plastic material.

The use of the spectacle frame is thus as follows: starting from the assembled condition, illustrated in FIG. 1, if the user wishes to disassemble said frame into its various components, he has to initially exert compression at the arms of the nose pad 23, thus disengaging the ends of the fifth groove 25 from the recesses 26a and 26b defined on the lower bar 4.

The user subsequently removes the insert 24 with an equally simple operation, by virtue of the deformability thereof.

The engagement means constituted by the second wing 19 are thus freed, and its shorter arm 20 can be disengaged from the third seat 21 defined on the lower bar.

In this manner, it is possible to remove the lens pair 6 from the first and second grooves 5a and 5b defined on the lower or upper bar or the single lens 7 if the elements 9a and 9b are not used.

After doing this, the user can mutually disengage the upper bar and the lower bar by sliding the first tabs 17a and 17b out of the second seats 16 defined at the ends of the upper bar 2 which are adjacent to the temples 3a and 3b.

It is thus possible to replace the lower bar 4 in order to change a color combination or adapt to the shape of new lenses to be applied.

If he wishes to use a single lens, the user can furthermore replace or remove the elements 9a and 9b by making them slide so as to disengage the pin 12 from the cavity 13 and thus disengage the lug 14 from the first groove 5a.

Reassembly of the spectacle frame occurs according to a pattern which is the reverse of the one described above.

It has thus been observed that the invention has achieved the intended aim and objects, a spectacle frame having been obtained which allows the rapid and easy disassembly of its various components, thus allowing the user to vary any color combinations or the type of lens to be used by changing, for example, only the lower bar.

This condition is advantageously very useful if the user wishes to change the type of lens according to specific uses, such as for example for use in conditions in which intense glare occurs, such as in the mountains or at the seaside, for use in conditions of normal glare, such as for example in town, or for special uses, such as optimum contrast in sports conditions, such as skiing, or for particular and special anti-misting lenses, which are available only for simple frames.

The replaceability of the elements 9a and 9b can furthermore be such as to allow to partially or fully close the openings 11, thus varying the ventilation of the frame according to the specific requirements.

The presence of the means for the mutual temporary safety locking of the second wing 19 and the lower bar 4 allow to put the spectacles on in conditions of maximum safety for the user.

The invention is naturally susceptible to numerous modifications and variations, all of which are within the scope of the same inventive concept.

The materials and the dimensions which constitute the individual components of the invention may also be the most pertinent according to the specific requirements

I claim:

1. Spectacle frame with detachable elements, comprising an upper bar to which two temples are hinged, said bar being laterally provided with first temporary engagement seats for possible elements for ventilation and connection to a pair of lenses, or for connection to a single lens, and with second temporary engagement seats for a lower supporting bar for said lens pair or single lens, engagement means bridging said upper and lower bars and removably engaging complementarily shaped grip means associated with one of said bar, means being provided for the temporary mutual safety locking of said engagement means and of said grip means.

2. Frame according to claim 1, wherein said upper bar is laterally provided, proximate to the end to which said two temples are hinged, with first temporary engagement seats for the end of elements for ventilation and connection to said lens pair, each of said elements being constituted by a body which has a plurality of openings, a protrusion extending from said body at the end which can be associated with said first seats, said protrusion being removably insertable in a complementarily shaped cavity defined within said first seats.

3. Frame according to claim 1, wherein a lug protrudes above said body and is slidingly associable at first grooves defined on said upper bar, a third groove for positioning the ends of said lens pair being defined on said body on the side opposite to sad protrusion.

4. Frame according to claim 3, wherein the ends of said single lens are associable with said first seats possibly by omitting said elements.

5. Frame according to claim 3, wherein said upper bar has, in a region adjacent to said first seats, second temporary engagement seats for the ends of said lower bar, a pair of first essentially T-shaped tabs protruding from said ends and slidingly engaging within said complementarily shaped second seats.

6. Frame according to claim 1, wherein engagement means protrude at the central region of said upper bar from the surface which faces the user's face, said engagement means being constituted by a second essentially L-shaped wing whose shorter arm is directed toward said lens pair or single lens.

7. Frame according to claim 6, wherein said second wing removably engages complementarily shaped grip means which are associated with, or defined at, said lower bar, said lower bar having, at said shorter arm of said second wing, a third seat which is shaped complementarily thereto, a fourth groove approximately equal in width to said second wing being defined transversely to said lower bar for the positioning of said second wing.

8. Frame according to claim 1, wherein said means for the temporary mutual safety locking of said second wing and of said lower bar are constituted by a nose pad and by an insert, said nose pad being provided by means of a soft polymer with which rubber is associated and makes contact with the user's nose, said nose pad being V-shaped and its wings being elastically compressible.

9. Frame according to claim 8, wherein said nose pad is provided with a fifth groove whose width is approximately equal to that of said lower bar, the interconnection between said lower bar and said nose pad occurring by virtue of the definition of a pair of recesses defined on said lower bar, the terminal ends of said nose pad interacting with said recesses at said fifth groove.

10. Frame according to claim 1, wherein said nose pad has a third planar tab which protrudes at the connecting point of said arms and abuts at said second tab.

11. Frame according to claim 1, wherein said insert can be arranged between said upper and lower bars at the region of mutual connection thereof by means of said second tab, said insert having such a shape as to conceal the interspace between said bars and said lens pair.

12. Frame according to claim 11, wherein said elastically deformable insert is provided with a body at whose ends a fourth tab and a fifth tab protrude and are temporarily insertable respectively at said first groove defined on said upper bar and at a second groove defined at said lower bar in the region which faces said second wing.

* * * * *